United States Patent [19]

Stadler et al.

[11] Patent Number: 4,609,657
[45] Date of Patent: Sep. 2, 1986

[54] ERGOT PEPTIDE ALKALOID DERIVATIVES, PROCESSES FOR THEIR PREPARATION AND PHARMACEUTICAL COMPOSITIONS CONTAINING THEM

[75] Inventors: Paul Stadler, Biel-Benken; Franz Troxler, Bottmingen, both of Switzerland

[73] Assignee: Sandoz Ltd., Basel, Switzerland

[21] Appl. No.: 168,567

[22] Filed: Jul. 14, 1980

Related U.S. Application Data

[63] Continuation of Ser. No. 3,757, Jan. 15, 1979, abandoned.

[30] Foreign Application Priority Data

Jan. 20, 1978 [CH] Switzerland ............... 622/78

[51] Int. Cl.$^4$ ............... A61K 31/48; C07D 519/02
[52] U.S. Cl. ............... 514/250; 544/346; 544/349; 560/60
[58] Field of Search ............... 544/346; 424/250, 261

[56] References Cited

U.S. PATENT DOCUMENTS

| | | | |
|---|---|---|---|
| 3,422,110 | 1/1969 | Stadler et al. | 544/346 |
| 3,586,683 | 6/1971 | Stadler et al. | 544/346 |
| 3,846,433 | 11/1974 | Stadler et al. | 544/346 |
| 4,145,549 | 3/1979 | Stadler | 544/346 |

FOREIGN PATENT DOCUMENTS

| | | |
|---|---|---|
| 1620386 | 8/1970 | Fed. Rep. of Germany . |
| 2700234 | 7/1977 | Fed. Rep. of Germany ...... 544/346 |
| 1149565 | 4/1969 | United Kingdom ............ 544/346 |

*Primary Examiner*—Alton D. Rollins
*Attorney, Agent, or Firm*—Gerald D. Sharkin; Robert S. Honor; Thomas O. McGovern

[57] ABSTRACT

This invention provides compounds of

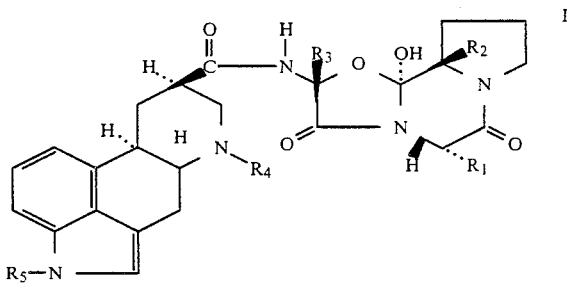

wherein $R_1$ is benzyl or benzyl substituted by hydroxy, chlorine, fluorine, amino, amido, $(C_{2-5})$ alkanoylamino, $(C_{1-4})$ alkyl, $(C_{1-4})$ alkylamino, $(C_{1-4})$ alkoxy, $(C_{1-4})$ alkylamido, di[$(C_{1-4})$ alkyl]amino, or di[$(C_{1-4})$ alkyl]amino, $R_2$, $R_4$ and $R_5$ are each $(C_{1-4})$ alkyl, and $R_3$ is $(C_{2-4})$ alkyl are prolactin secretion promoters.

10 Claims, No Drawings

ERGOT PEPTIDE ALKALOID DERIVATIVES, PROCESSES FOR THEIR PREPARATION AND PHARMACEUTICAL COMPOSITIONS CONTAINING THEM

This is a continuation of application Ser. No. 003,757, filed Jan. 15, 1979, now abandoned.

This invention relates to ergot peptide alkaloid derivatives, processes for their preparation and pharmaceutical compositions containing them.

The present invention provides compounds of formula I

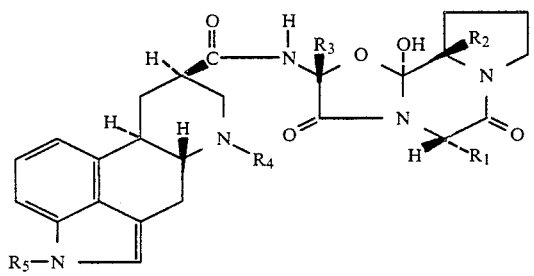

wherein $R_1$ is benzyl or benzyl substituted by hydroxy, chlorine, fluorine, amino, amido, $(C_{2-5})$alkanoylamino, $(C_{1-4})$alkyl, $(C_{1-4})$alkylamino, $(C_{1-4})$alkoxy, $(C_{1-4})$alkylamido, di[$(C_{1-4})$alkyl]amino, or di[$(C_{1-4})$alkyl]amido, $R_2$, $R_4$ and $R_5$ are each $(C_{1-4})$alkyl, and $R_3$ is $(C_{2-4})$alkyl.

Alkanoyl preferably has 2 carbon atoms. Each other moiety containing 1–4 carbon atoms preferably has 1 carbon atom. When $R_1$ is dialkylamino or dialkylamido, the alkyl groups may be the same or different. Conveniently however, they are the same. $R_3$ is preferably branched and is for example isopropyl. $R_1$ is conveniently benzyl, which may be mono-substituted. Preferably $R_1$ is benzyl.

The present invention also covers a process for the production of a compound of formula I which comprises condensing an acid addition salt of a compound of formula II

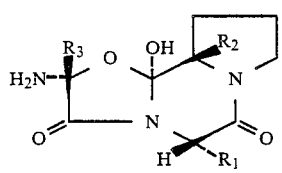

wherein $R_1$, $R_2$ and $R_3$ are as defined above, with a reactive acid derivative of a compound of formula III

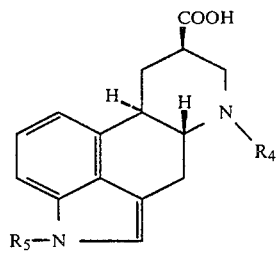

wherein $R_4$ and $R_5$ are as defined above.

The process may be effected in analogous manner to those used to produce known ergot peptide alkaloids by condensation.

The reactive acid derivative of a compound of formula III may be formed in situ. Preferably the addition product of a compound of formula III with dimethyl formamide or dimethyl acetamide, and oxalyl chloride is used. Preferably the reaction is effected in the presence of triethylamine or pyridine. Conveniently the free base form of a compound of formula II is formed in situ by reacting the acid addition salt form with a base. Suitable solvents are for example chloroform, methylene chloride, dimethyl formamide or acetonitrile.

Suitable temperatures are between $-30°$ and $+20°$ C.

The compounds of formula II are new and from part of the invention. In accordance with the invention an acid addition salt of a compound of formula II may be produced by splitting off the protecting group in a compound of formula IV

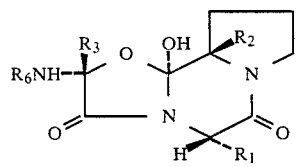

wherein $R_1$, $R_2$ and $R_3$ are as defined above, and $R_6$ is a protecting group in the presence of an acid.

The process may be effected in analogous to known methods for splitting off protecting groups from analogous base—sensitive peptides, for example by hydrogenolysis. Preferably the protecting group is benzyloxycarbonyl. Conveniently the acid is a mineral acid such as hydrochloric acid.

A compound of formula IV wherein $R_6$=benzyloxycarbonyl may be produced by converting a compound of formula V

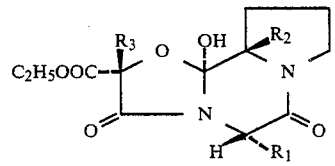

in known manner into the corresponding acid, which in term is converted into the corresponding acid chloride, which is converted via the acid azide into the corresponding benzyloxycarbonylamino compound.

A compound of formula V may be produced by reacting a compound of formula VI

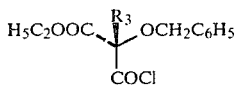

with a compound of formula VII

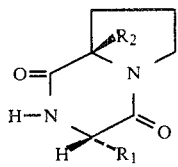

and finally hydrogenating the resulting compound of formula VIII

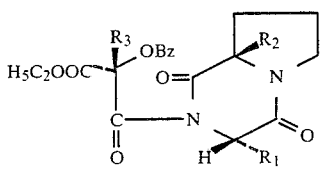

In so far as the preparation of any starting material is not particularly described these are known or may be made in known manner used for the preparation of analogous compounds.

Free base forms of the compound of formula I may be converted into acid addition salt forms and vice versa. Suitable salts include the hydrochloride and methanesulphonate.

In the following examples all temperatures are in degrees Centigrade and are uncorrected.

EXAMPLE 1,10'αβ-dimethyl-9,10-dihydro-ergocristine

[In formula I $R_1=CH_2.C_6H_5$, $R_2=R_4=R_5=CH_3$, $R_3=CH(CH_3)_2$]

5.08 g (0.04 mole) oxalyl chloride in 7 ml absolute acetonitrile are added dropwise within 10 minutes to 100 ml absolute dimethylformamide at −20° C. The resultant yellow suspension is treated after 10 minutes at −20° with 11.35 g (0.04 mole) 1-methyl-9,10-dihydrolysergic acid. The mixture is stirred for 30 minutes at from −10° to 0° and then cooled to −20°. 40 ml absolute pyridine at −20° are then added as quickly as possible followed by 9.65 g (0.02 mole) (2R, 5S, 10aS,10bS)-2-amino-2-isopropyl-5-benzyl-10b-hydroxy-10a-methyl-3,6-dioxo-octahydro-oxazolo[3,2-a]pyrrolo[2,1-c]pyrazine hydrochloride, obtained in step (e) hereinafter. The mixture is stirred for 2 hours at 0° to finish the reaction, then cooled to −15°, and treated with 40 ml citrate buffer (pH 4), the buffer being added at such a rate that the temperature does not rise above −15°. 2N sodium carbonate solution is added and the mixture is extracted with methylene chloride. The estracts are dried, evaporated in a vacuum to give a crystalline crude product which is chromatographed in a 10 fold amount of alumina (activity II). Elution with methylene chloride yields an almost colourless product which after recrystallization from methylene chloride/ethanol yields the title compound. M.Pt. 202°–203° (decomp) $[\alpha]_D^{20} = +2.9°$ (c=1.6 $CH_2Cl_2$).

The starting material of formula II may be produced as follows:

(a) (2'S, 3S, 9S)-2-(2'-benzyloxy-2'-isopropyl-O-ethylmalonyl)-1,4-dioxo-3-benzyl-9-methyl-octahydropyrrolo[1,2-a]pyrazine A suspension of 67.8 g L-phenylalonyl-L-α-methylproline lactam [[α]$_D^{20}$ = −86° (c=1, $C_2H_5OH$)] in 40 ml absolute pyridine and 35 ml absolute dioxane is cooled to 0°. This is stirred and treated over 5 minutes 74.8 g S-(+)isopropyl-benzyloxy-malonic acid monoethyl ester chloride, the temperature being from 0° to 5°. The resultant nitrile suspension is warmed to 60° within 20 minutes and is maintained at this temperature for 7 hours. The mixture is poured onto ice, made acid with 2N HCl and extracted with ether. The extracts are washed with ice-water, sodium hydrogen carbonate solution and again with ice-water. The solution is dried well with $Na_2SO_4$ and the solvent is carefully removed, finally in a high vacuum to leave the heading compound as an orange foam in crude form.

(b) (2R, 5S, 10aS, 10bS)-2-ethoxycarbonyl-2-isopropyl-5-benzyl-10b-hydroxy-10a-methyl-3,6-dioxo-octahydro-oxazolo[3,2-a]pyrrolo[2,1-c]pyrazine 132 g of the crude ester of step (a) in 1800 ml ethanol in the presence of 35 g palladium on active charcoal (10% palladium) as catalyst are hydrogenated at 40°–42° and at normal pressure for 20 hours. The mixture is filtered and the filtrate evaporated in a vacuum to give the heading compound. M.Pt. 105°–107° (from isopropyl ether/$CH_2Cl_2$) $[\alpha]_D^{20} = +48.3°$ (c=1, $C_2H_5OH$)

(c) (2R, 5S, 10aS, 10bS)-2-carboxy-2-isopropyl-5-benzyl-10b-hydroxy-10a-methyl-3,6-dioxo-octahydro-oxazolo[3,2-a]pyrrolo[2,1-c]pyrazine 43 g of the compound of step (b) in 105 ml 2N NaOH are maintained at room temperature for 6 hours. The resultant clear solution is adjusted to pH 7 with 26.5 ml 4N HCl and extracted twice with ethyl acetate. The aqueous phase is adjusted to ca pH 1 with 26.5 ml 4N HCl, cooled in an ice-bath whereupon the heading compound crystallizes out, and is obtained after filtration and washing with a little ice-water in a form containing per mole 1 mole of water of crystallization. M.Pt. 116°–118° (decomp); $[\alpha]_D^{20} = +25°$ (c=1, $C_2H_5OH$)

(d) (2R, 5S, 10aS, 10bS)-2-N-benzyloxycarbonyl-amino-2-isopropyl-5-benzyl-10b-hydroxy-10a-methyl-3,6-dioxo-octahydro-oxazolo[3,2-a]pyrrolo[2,1-c]pyrazine 12.7 g oxalyl chloride in 20 ml absolute chloroform are added dropwise over 10 minutes to a mixture of 9.12 g absolute dimethylformamide and 50 ml absolute chloroform at −25°. The resultant clear, colourless solution is stirred for 10 minutes at about −10° and then treated with 21 g of the product of step (c) and 50 ml absolute chloroform. The mixture is maintained for 10 minutes at −10° to −15°, giving a clear solution of the corresponding acid chloride. The mixture is then cooled to −25° and stirred vigorously. 13 g of sodium azide in 40 ml water are added in single amount to the stirred mixture, which is stirred intensively for 3 minutes at −5° to 0°. 250 ml of 20% (w/w) potassium hydrogen carbonate solution is then added carefully and the mixture is extracted three times with cold chloroform. The organic phases are well dried with sodium sulphate, and the filtered clear solution is reduced in volume to about 250 ml at a maximum temperature of 25°. 10.8 g benzyl alcohol and 1 drop of concentrated hydrochloric acid are added to the mixture which is then boiled for 40 minutes under reflux. The mixture is evaporated under a water pump vacuum and finally a high vacuum at 90° to give title compound as the residue. M.Pt. 176°–178° (CH$_2$Cl$_2$/ethyl acetate) $[\alpha]_D^{20} = +37°$ (c=2, C$_2$H$_5$OH)

(e) 2R, 5S, 10aS, 10bS)-2-amino-2-isopropyl-5-benzyl-10b-hydroxy-10a-methyl-3,6-dioxo-octahydro-oxazolo[3,2-a]pyrrolo[2,1-c]pyrazine hydrochloride 40.6 g of the product of step (d) in a mixture of 120 ml absolute dimethylformamide, 275 ml absolute tetrahydrofuran and 18.5 ml 5.6N HCl in tetrahydrofuran in the presence of a 10% palladium/active charcoal (10% palladium) are hydrogenated at 20° and at normal pressure. After the mixture is stirred for 10 minutes vigorously the hydrogen uptake of 1.75 liters is complete. The catalyst is filtered off and the colourless solution is evaporated in a vacuum to a viscous oil. The oil is taken up in 40 ml absolute tetrahydrofuran and 100 ml absolute ether. The heading compound crystallises out, is filtered off, washed with a mixture of 1 part tetrahydrofuran and 2 parts ether and then dried in a high vacuum at 20° to give a form containing per mole 1 mole of dimethylformamide as solvent of crystallization. M.Pt. 107°–109° (decomp) $[\alpha]_D^{20} = +19.8°$ (c=1, DMF)

In analogous manner to that described in Example 1, from the corresponding starting material of formula II obtained according to steps (a)–(e) above the following compounds of formula I are obtained wherein R$_2$=R$_3$=R$_4$=R$_5$=n-butyl and R$_1$ is

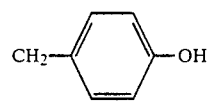 (i)

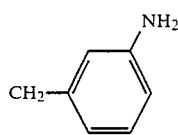 (ii)

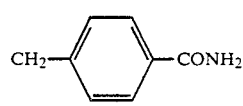 (iii)

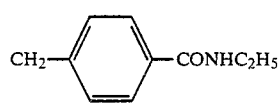 (iv)

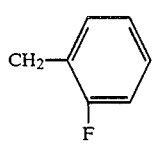 (v)

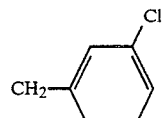 (vi)

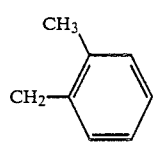 (vii)

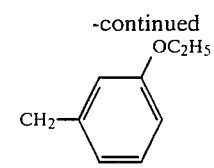 (viii)

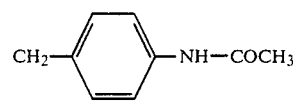 (ix)

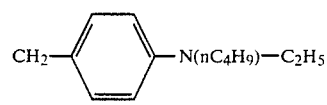 (x)

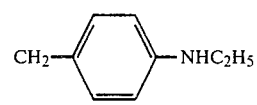 (xi)

and

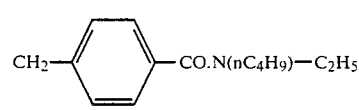 (xii)

The compound of formula I are useful because they exhibit pharmacological activity. In particular they stimulate prolactin secretion as indicated in standard tests on administration of from 0.1 to 10 mg/kg s.c. of the compounds, wherein an increase in prolactin concentration in the serum is determined by radioimmunoassay. Additionally the stimulating effect may be confirmed by an induction of pseodogravity in female adult rats doses of from 0.25 to 5.0 mg/kg s.c.

The compounds are therefore useful as inhibitors of fertility.

The compounds also exhibit a puberty inducing effect as indicated in standard tests. For example in young female rats (ca 40 g) an induction in puberty are observed after a 5 day treatment of the compounds administered orally twice a day in doses of 3 mg/kg per animal.

The compounds are therefore useful in the treatment of Pubertas tarda.

The compounds also exhibit a mammotropic effect as indicated in standard tests. For example in female adult rats pretreated with oestrogen an administration of the compounds at a dose of 3 mg/kg s.c. twice daily leads to a mammotropic effect after 10 days.

The compounds are therefore useful in the treatment of insufficient milk formation.

For the above mentioned uses the dosage will, of course, vary depending on the compound employed, mode of administration and therapy desired. However, in general, satisfactory results are obtained with administration at a daily dosage of from 0.05 mg to about 100 mg per kg animal body weight, conveniently given in divided doses 2 to 4 times a day or insustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

The compounds of formula I may be administered in free form or in pharmaceutically acceptable acid addition salt form. These salt forms have the same order of activity as the free base form. The present invention provides a pharmaceutical composition comprising a compound of formula I in free base form or in pharmaceutically acceptable acid addition salt form in association with a pharmaceutical carrier or diluent. Such compositions may be formulated in conventional manner so as to be for example a solution capsule or tablet.

In a group of compounds $R_1$ is benzyl or benzyl substituted by hydroxy, amino, chlorine, fluorine, alkyl, alkoxy, alkanoylamino or dialkylamino, $R_4$ and $R_5$ are each alkyl, $R_2$ is methyl and $R_3$ is isopropyl.

As will be appreciated by one skilled in the art by virtue of the functional groups, e.g. the amino group, present in a compound of formula II, they may be used to prepare a wide variety of ergot peptide alkaloids. For example an ergot peptide alkaloid having a 10'a ($C_{1-4}$)alkyl group and a 2'-($C_{2-4}$)alkyl group may be made by condensing a compound of formula II with a reactive acid derivative of a lysergic acid and where required converting the resulting product into an ergot peptide alkaloid having a 10'a ($C_{1-4}$)alkyl group and a 2'-($C_{2-4}$)alkyl group.

What we claim is:

1. A compound of formula I

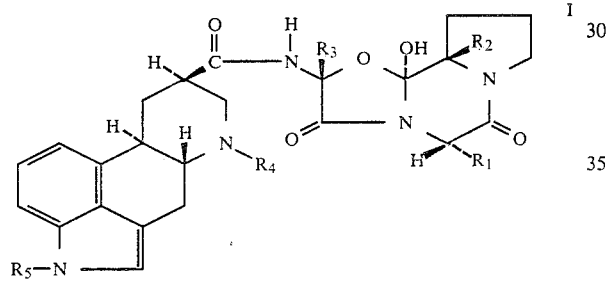

wherein $R_1$ is benzyl or benzyl substituted by hydroxy, chlorine, fluorine, amino, amido, ($C_{2-5}$)alkanoylamino, ($C_{1-4}$)alkyl, ($C_{1-4}$)alkylamino, ($C_{1-4}$)alkylamido, di[($C_{1-4}$)alkyl]amino, or di[($C_{1-4}$)alkyl]amido, $R_2$, $R_4$ and $R_5$ are each ($C_{1-4}$)alkyl, and $R_3$ is ($C_{3-4}$) branched chain alkyl or a pharmaceutically acceptable acid addition salt thereof.

2. The compound of claim 1 which is 1,10'aβ-dimethyl-9,10-dihydro-ergocristine.

3. A compound of claim 1 wherein $R_1$ is benzyl or benzyl substituted by hydroxy, amino, chlorine, fluorine, alkyl, alkanoylamino or dialkylamino, $R_4$ and $R_5$ are each alkyl, $R_2$ is methyl and $R_3$ is isopropyl.

4. A compound of claim 3 wherein $R_1$ is benzyl.

5. A pharmaceutical composition useful in stimulating prolactin secretion which comprises a therapeutically effective amount of a compound of claim 1 in association with a pharmaceutical carrier or diluent.

6. A method of stimulating prolactin secretion in animals which comprises administering to an animal in need of said treatment a therapeutically effective amount of a compound of formula I

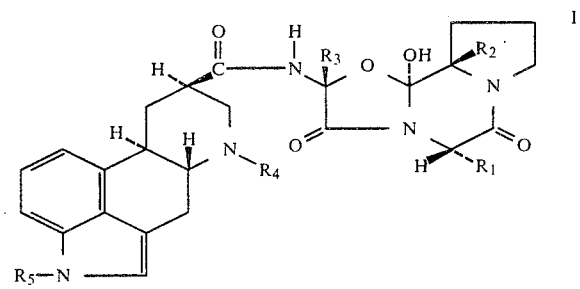

wherein $R_1$ is benzyl or benzyl substituted by hydroxy, chlorine, fluorine, amino, amido, ($C_{2-5}$)alkanoylamino, ($C_{1-4}$)alkyl, ($C_{1-4}$)alkylamino, ($C_{1-4}$)alkoxy, ($C_{1-4}$)alkylamido, di[($C_{1-4}$)alkyl]amino, or di[($C_{1-4}$)alkyl]amido, $R_2$, $R_4$ and $R_5$ are each ($C_{1-4}$)alkyl, and $R_3$ is ($C_{2-4}$)alkyl, or a pharmaceutically acceptable acid addition salt thereof.

7. A compound of formula II

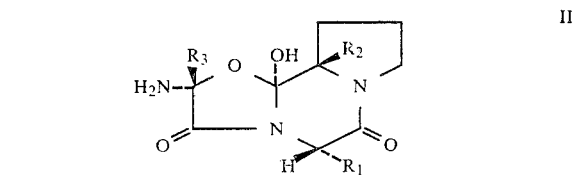

wherein $R_1$ is benzyl or benzyl substituted by hydroxy chlorine, fluorine, amino, amido, ($C_{2-5}$)alkanoylamino, ($C_{1-4}$)alkyl, ($C_{1-4}$)alkylamino, ($C_{1-4}$)alkylamido, di[($C_{1-4}$)alkyl]amino, or di[($C_{1-4}$)alkyl]amido, $R_2$ is ($C_{1-4}$)alkyl, and $R_3$ is ($C_{3-4}$) branched chain alkyl, or an acid addition salt thereof.

8. A compound of claim 7 which is (2R, 5S, 10aS, 10bS)-2-amino-2-isopropyl-5-benzyl-10b-hydroxy-10a-methyl-3,6-dioxo-oxtahydro-oxazolo[3,2-a]pyrrolo[2,1-c]pyrazine.

9. A compound of claim 7 wherein
$R_1$ is benzyl or benzyl substituted by hydroxy, amino, chlorine, fluorine, alkyl, alkanoylamino or dialkylamido,
$R_2$ is methyl and $R_3$ is isopropyl.

10. A compound of claim 7 wherein $R_1$ is benzyl.

* * * * *